(12) United States Patent
Yarwood et al.

(10) Patent No.: US 6,726,928 B2
(45) Date of Patent: *Apr. 27, 2004

(54) PROCESS FOR PREPARING SOLID DOSAGE FORMS FOR UNPALATABLE PHARMACEUTICALS

(75) Inventors: Richard J. Yarwood, Collingbourne Kingston (GB); Patrick Kearney, Swindon (GB); Andrew R. Thompson, Swindon (GB)

(73) Assignee: R.P. Scherer Technologies, Inc., Paradise Valley, NV (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/551,361

(22) Filed: Apr. 18, 2000

(65) Prior Publication Data

US 2002/0142038 A1 Oct. 3, 2002

Related U.S. Application Data

(63) Continuation-in-part of application No. 09/026,561, filed on Feb. 20, 1998, now abandoned, which is a continuation-in-part of application No. 08/330,936, filed on Oct. 28, 1994, now Pat. No. 5,738,875.

(51) Int. Cl.$^7$ ............................... A61K 9/20; A61K 9/36; A61K 9/14; A61K 9/16; A61K 9/00

(52) U.S. Cl. .................. 424/464; 424/480; 424/484; 424/485; 424/488; 424/489; 424/494

(58) Field of Search ......................... 424/484, 464, 424/485, 488, 489, 480, 494

(56) References Cited

U.S. PATENT DOCUMENTS

| | | | |
|---|---|---|---|
| 4,305,502 A | 12/1981 | Gregory et al. | 206/532 |
| 4,855,326 A | 8/1989 | Fuisz | 514/777 |
| 5,039,540 A | 8/1991 | Ecanow | 426/385 |
| 5,188,825 A | 2/1993 | Iles et al. | 424/78.1 |
| 5,206,025 A | 4/1993 | Courteille et al. | 424/439 |
| 5,298,261 A | 3/1994 | Pebley et al. | 424/488 |
| 5,330,763 A | 7/1994 | Gole et al. | 424/484 |
| 5,330,764 A | 7/1994 | Gole et al. | 424/484 |
| 5,382,437 A | 1/1995 | Ecanow | 424/499 |
| 5,853,762 A | 12/1998 | Myers et al. | 424/488 |

*Primary Examiner*—Shelley A. Dodson
(74) *Attorney, Agent, or Firm*—Donald O. Nickey

(57) ABSTRACT

A process for the preparation of a rapidly disintegrating dosage form a pharmaceutically active substance which has an unacceptable taste wherein there is formed a solution or a suspension in a solvent of a form of the pharmaceutically active substance which is less soluble in water and more palatable than the form with the unacceptable taste together with a water-soluble or water-dispersible carrier material. Discrete units of the suspension or solution are formed and the solvent is removed from the discrete units under conditions whereby a network of the carrier material carrying a dosage for the less soluble and more palatable form of the pharmaceutically active substance is formed.

17 Claims, No Drawings

PROCESS FOR PREPARING SOLID DOSAGE FORMS FOR UNPALATABLE PHARMACEUTICALS

RELATED APPLICATIONS

The present application is a continuation-in-part of application Ser. No. 09/026,561 filed Feb. 20, 1998 now abandoned, which is a continuation of application Ser. No. 08/330,936 filed Oct. 28, 1994, now U.S. Pat. No. 5,738,875 which issued Apr. 14, 1998. These applications and patents are incorporated herein by reference.

FIELD OF THE INVENTION

The present invention relates to a process for preparing solid pharmaceutical dosage forms and, in particular, to a process for preparing a solid, oral, rapidly disintegrating dosage form of a pharmaceutically active substance which has an unpleasant taste.

BACKGROUND OF THE INVENTION

Many pharmaceutically active substances are presented for oral administration in the form of conventional oral dosage forms, including tablets, pills or capsules. The tablet, pill or capsule generally has to be swallowed with water so that the pharmaceutically active substance can be absorbed via the gastrointestinal tract. For some patients, swallowing the tablet, pill or capsule is difficult or impossible and this is particularly the case for pediatric patients and geriatric patients. A similar difficulty is often encountered when trying to administer tablets to non-human animals which may be uncooperative in taking tablets, pills or capsules.

Oral solid pharmaceutical dosage forms which rapidly disintegrate in the mouth and methods for their preparation have been proposed in GB-A-1548022 and GB-A-2111423. The solid dosage forms, as disclosed in these references, comprise an open matrix network carrying the pharmaceutically active substance, the open matrix comprising a water-soluble or water-dispersible carrier material which is inert towards the pharmaceutically active substance. The solid dosage forms are prepared by the sublimation or removal of solvent from a solution or suspension comprising the pharmaceutically active substance and the carrier material. Sublimation or removal of solvent is preferably carried out by freeze drying.

U.S. Pat. No. 5,382,437 to Ecanow discloses a readily dissolved carrier composition suitable for use in administration of drugs and foodstuffs. The composition comprises a skeletal structure produced by contacting a gel and a rigidifying material for the gel with liquified ammonia at low temperature until the mass solidifies. As the mass is slowly warmed to ambient temperature under vacuum, the solid ammonia sublimes from the solid state to the gas state to provide a porous drug or foodstuff delivery system.

Other methods for the preparation of oral solid pharmaceutical dosage forms which rapidly disintegrate in the mouth are disclosed in U.S. Pat. Nos. 4,855,326; 5,039,018; 5,120,549; 5,330,763; PCT/JP93/01631; PCT/US93/125661 and WO 98/57648, which are incorporated herein by reference.

The solid dosage forms which are produced by these various methods rapidly disintegrate on being placed in the mouth of the patient, thereby delivering the desired dose of the pharmaceutically active substance.

Although the solid dosage forms as described above overcome the problems of swallowing tablets, pills or capsules, the patient will taste the pharmaceutically active substrate as the dosage form disintegrates. For some pharmaceutically active substances, the taste, if slightly unpleasant, can be rendered acceptable by the use of sweetening agents, flavoring agents and the like, which mask the taste. Yet, in some pharmaceutically active substances, the unpalatable taste will still exist, despite the use of sweetening agents and flavoring agents. In those instances in which over-flavoring techniques alone will not suffice, the insolubilization techniques of the present invention can result in palatable formulations.

SUMMARY OF THE INVENTION

Through the efforts of the present inventors, a new method for the preparation of a solid, oral, rapidly disintegrating dosage form of a pharmaceutically active substance which has an unacceptable taste has been developed, which does not wholly depend upon trying to mask the unacceptable taste by the use of sweetening agents, flavoring agents and the like. In general, the present invention uses the less soluble form to the drug to reduce or eliminate the use of sweetening agents, flavor and the like.

In a first aspect, the present invention provides a process for the preparation of a solid, oral, rapidly disintegrating dosage form of a pharmaceutically active substance which has an unacceptable taste. The process comprises forming a solution or a suspension in a solvent of a form of the pharmaceutically active substance which is less soluble in water than the form with the unacceptable taste, together with a water-soluble or water-dispersible carrier material, forming discrete units of the solution or suspension. The solvent is then removed from the discrete units under conditions whereby a network of the carrier material carrying a unit dosage of the less soluble form of the pharmaceutically active substance is formed.

In another aspect, the invention provides a rapidly disintegrating dosage form of a pharmaceutically active substance when prepared by the process of the invention.

The present invention also includes within its scope, a solid, oral, rapidly disintegrating dosage form of a pharmaceutically active substance which has been rendered more palatable by the process as described above.

The present invention is also directed to a solid, oral, rapidly disintegrating dosage form comprising loperamide free base as the pharmaceutically active substance in a network of a carrier material selected from the group consisting of water-soluble and water-dispersible carrier materials.

Further, the invention discloses a solid, oral, rapidly disintegrating dosage form comprising domperidone free base as the pharmaceutically active substance in a network of a carrier material selected from the group consisting of water-soluble and water-dispersible carrier materials.

DETAILED DESCRIPTION OF THE INVENTION

As used herein and in the claims, the term "rapidly disintegrating" means that the solid dosage form will disintegrate in water at 37° C. in 60 seconds or less, preferably 5 to 10 seconds or less, when tested by the following procedure which is analogous to the Disintegration Test for Tablets, B.P. 1973 and which is further described in British Patent No. 1548022.

Disintegration Test—Apparatus

A glass or suitable tube 80 to 100 mm long, with an internal diameter of about 38 mm and an external diameter of 30 to 31 mm and fitted at the lower end so as to form a basket, with a disc or rustproof wire gauze complying with the requirements for a No. 1.70 sieve (B.P. 1983, page A136).

A glass cylinder with a flat base and an internal diameter of about 45 mm containing water and not less than 15 cm deep at a temperature between 36° C. and 38° C.

The basket is suspended centrally in the cylinder in such a way that it can be raised and lowered repeatedly in a uniform manner so that at the highest position, the gauze just breaks the surface of the water and at the lowest position, the upper rim of the basket just remains clear of the water.

Method

Place one shaped article (the rapidly disintegrating dosage form) in the basket and raise and lower it in such a manner that the complete up and down movement is repeated at a rate equivalent to thirty times a minute. The shaped articles are considered disintegrated when no particle remains above the gauze which would not readily pass through it.

On oral administration of the solid dosage form of the invention to a patient, the pharmaceutical dosage form rapidly disintegrates in the mouth. The rapidly disintegrating dosage form of the present invention enables poorly tasting pharmaceutically active substances to be presented in a palatable form without changing the bioavailability of the pharmaceutically active substance relative to an existing solid dosage form (i.e., pills and tablets) containing the more soluble compound. The pharmaceutically active substance is presented as a less soluble form rendering less of the drug to be tasted as the solid dosage form dissolves disintegrates in the saliva.

The pharmaceutically active substance with the unacceptable taste may be presented in less soluble form prior to formation of the solution or suspension. Alternatively, the pharmaceutically active form may be converted into the less soluble form during the process of the invention, for example during the preparation of the solution or suspension.

The pharmaceutically active substance with the unacceptable taste may be rendered less soluble by conversion of a salt to a free acid or a free base, or conversion of a free base to a salt, or changing the salt form to a less soluble salt form, or by using the common ion effect or salting out, or changing the polymorphic form thereof, or by adjusting the pH, or by any other suitable means. Each of these conversion approaches may be carried out using methods well known to persons of ordinary skill in this art. In the publication "Pharmaceutics—The Science of Dosage Form Design"; Ed. M. E. Aulton, Churchill Livingstone provides a general discussion of methods for conversion of drugs to forms of different solubility. The teachings of this reference are incorporated herein by reference.

The conversion of a salt to a free acid or free base may be carried out, for example, by the addition of an amount of acidic or alkaline agent to the salt and mixing of the resultant suspension until the solid salt has been neutralized to the free base form. The salt may be dispersed in an appropriate amount of water along with the acidic or alkaline agent and any other excipients required to produce the dosage form. This mixture is then mixed continuously until the solid salt has been converted to the respective free base or free acid. The amount of acidic or alkaline agent needed is determined experimentally by preparing formulations with varying amounts of the agent and performing taste assessments on the finished product.

As a typical example of a salt to a free base, the hydrochloride salt, e.g. Loperamide hydrochloride, may be converted to the free base using a bicarbonate buffer, such as for example sodium hydrogen carbonate buffer.

Conversion of a salt form to a less soluble salt form may be achieved by dispersing the salt in an aqueous medium and then adding the required amount of an appropriate excipient salt. An appropriate excipient salt is one which contains a counter-ion of opposite charge to the dissolved drug and which has a stronger affinity for the drug than the counter-ion in the original drug salt. This mixture is agitated until the conversion is complete. The amount of acidic or alkaline agent needed is determined experimentally by preparing formulations with varying amounts of the agent and performing taste assessments on the finished product Pages 227–229 of Pharmaceutics, supra, illustrates methods for calculation of the pH of a drug, the susceptibility of that drug to salt formation and the type of salt that can be formed. Examples of pharmaceutically acceptable salts are hydrochloride, sulfate, besylate, maleate, tartrate, benzoate and citrate. By way of example of the effect of a particular salt form on solubility, for the drug Chlordiazepoxide, the following illustrates the differences in solubility of the different salts of the drug. Chlordiazepoxide sulfate or besylate are freely soluble whereas Chlordiazepoxide base has a solubility of about 2.0 mg ml$^{-1}$. Chlordiazepoxide maleate has a higher solubility of about 57.1 mg ml$^{-1}$ whereas Chlordiazepoxide tartrate has a solubility of 17.9 mg ml$^{-1}$, Chlordiazepoxide benzoate has a solubility of 6.0 mg ml$^{-1}$ and Chlordiazepoxide acetate has a solubility of 4.1 mg ml$^{-1}$.

The common ion effect or salting out may be used to reduce the solubility. This is achieved by the addition of a soluble electrolyte if this contains a common ion to the drug to be dissolved. In effect, the drug and the additional electrolyte are competing for the solvent, which in turn reduces the solubility of the drug. An example of the common ion effect (or salting out) is the addition of sodium bromide to a near-saturated solution of dextromethorphan hydrobromide to effect precipitation of at least a portion of the drug. The effect may be explained with reference to the solubility product, the constant equilibrium value of the product of the concentrations of the two ionic species arising from the drug. An added excess of one ion in the form of a soluble salt will cause the solubility product to be exceeded, and this will be corrected by removal of a proportion of both drug ions by precipitation of solid drug.

The formation of a hydrate is typically achieved by stirring a suspension of the drug in water to effect conversion of the drug to the hydrate. Piroxicam monohydrate is produced progressively when a suspension of anhydrous piroxicam is stirred in water.

The polymorphic form may be changed in order to present the pharmaceutically active substance with the unacceptable taste in less soluble form prior to formation of the solution or suspension. Polymorphs are solid materials with at least two different molecular arrangements, each of which has a distinct crystal structure. The particular crystal state of a solid depends, at least in part, on the solvent(s) used for recrystallization. Different polymorphic forms have different stabilities, different oral bioavailabilities and different solubilities. A discussion of the phenomenon of polymorphism appears in WO 98/57648. The solubility of a crystalline form generally decreases with the increase in melting point of the crystalline form. Inter-conversion of polymorphs can occur spontaneously. The selection of a less soluble polymorph can also be carried out by solvent manipulation, or by thermal techniques, notably sublimation and recrystallization from the melt. These techniques are well known to persons of ordinary skill in this art.

The solubility of weak acids and weak bases may be adjusted by pH control. Increasing the pH of a solution can decrease solubility of a weak base, whereas the solubility of a weak acid can be decreased by a pH decrease. The relative levels of weak acid or weak base added to the drug can be calculated with the knowledge of the Henderson-Hasselbalch equation, and by calculation of the $pK_a$ of the drug concerned in the solvent in question.

For example, where Piroxicam is the drug of interest, the pH may be adjusted in a manner which changes the ratio of the un-ionized to ionized species, which in turn provides for an approximately tenfold decrease in solubility, and a significant reduction in the bitter taste of the drug. Piroxicam (Feldene) has a "U"-shaped pH solubility curve with a minimum around pH 3.5. Typically, when Piroxicam is used in the system of the present invention, it exhibits a pH of about 6.5. This may be adjusted to approximately 4.0 by addition of an acid such as citric acid to produce the approximately tenfold decrease in solubility. This results in a significantly reduced bitter taste by reducing the amount of dissolution in the mouth. A further advantage arising out of the reduced solubility of Piroxicam is reduced formation of the hydrate which has a bright yellow color.

Other ways of rendering the pharmaceutically active form less soluble are reducing the solubility of highly hydrophilic drugs in the presence of an organic co-solvent. Bulking with less hydrophilic water-soluble solutes may have a similar effect.

The discrete units of the suspension or solution may be in the form of liquid units, for example contained within the pockets of a suitable mold. The liquid units may alternatively be in the form of gelled units where the carrier material readily forms a gel. These liquid units are then preferably frozen and the solvent removed via freeze drying. The removal of solvent from the discrete units comprising the pharmaceutically active substance in its less soluble form and a water-soluble or water-dispersible carrier material may also be carried out by other techniques well known to those skilled in the art. When the discrete units are in liquid form, they will generally be frozen or gelled prior to drying.

The liquid solution or suspension which may be contained within the pockets of a suitable mold is frozen, for example by passing a gaseous cooling medium, such as liquid nitrogen over the mold, or by inserting the mold into a nitrogen spray freezing chamber, or cooling by passing the mold over a cold surface. Once the dosage forms have been frozen, the mold may be stored in a cold store, prior to drying. Frozen discrete units may be dried by freeze drying according to techniques which are well known in the art. The solvent is sublimed in a freeze drying process under a reduced pressure which transforms the solid solvent directly into a vapor. The freeze drying process will generally be carried out in a freeze drying chamber typically operating under a vacuum of 0.1 to 1.0 mbar for a period of time of from 180 to 500 minutes.

Alternatively, frozen discrete units may be dried by a process as described in U.S. Pat. Nos. 5,120,549 and 5,330,763. In this method, the pharmaceutically active substance and carrier material dispersed in a first solvent is solidified and the solidified matrix is subsequently contacted with a second solvent that is substantially miscible with the first solvent at a temperature lower than the solidification point of the first solvent, the matrix component being substantially insoluble in the second solvent, the first solvent thereby being removed from the matrix.

Another alternative process for drying frozen discrete units is described in WO94/14422. In this process the solvent is removed under conditions whereby the solvent is evaporated from the solid through the liquid phase to a gas, rather than subliming from a solid to a gas as in lyophilization. This is achieved by vacuum drying at a temperature below the equilibrium freezing point of the composition at which point the solvent (such as water) changes phase.

When the discrete units are gelled units, any drying method can be used which does not affect the properties of the preparations. For example, drying may be carried out at decreased pressure, or by forced-air drying. Drying at decreased pressure is preferably carried out at a temperature of from 25° to 35° C. under a vacuum of −750 mm Hg or less, for 2 to 5 hours, while drying using forced-air drying is preferably carried out at a temperature of from 30 to 15° C. for 1 to 6 days.

The solvent used in forming the solution or suspension of the pharmaceutically active substance is preferably water but it may be admixed with a co-solvent, such as alcohol, if it is desired to improve the solubility of the active substance.

The carrier material which is used to form the network containing the pharmaceutically active substance may be any water-soluble or water-dispersible material that is pharmaceutically acceptable, inert to the pharmaceutically active substance and which is capable of forming a rapidly disintegrating network. The preferred carrier material for use in the present invention is gelatin, preferably pharmaceutical grade gelatin.

Other materials may also be used, for example hydrolyzed dextrose, dextran, dextrin, maltodextrin alginates, hydroxyethylcellulose, sodium carboxymethylcellulose, microcrystalline cellulose, corn-syrup solids, pectin, carrageenan, agar, chitosan, locust bean gum, xanthan gum, guar gum, acacia gum, tragacanth, konjac flour, rice flour, wheat gluten, sodium starch glycolate, soy fiber protein, potato protein, papain, horse radish peroxidase, glycine or mannitol.

The suspension or solution prepared according to the process of the present invention is preferably formed into discrete units by introduction into a mold which preferably comprises a plurality of depressions, each depression being of the desired shape and size for the oral dosage form product. The mold preferably comprises a plurality of depressions formed in a sheet of a filmic material which may be similar to the material employed conventionally in the blister packaging of pharmaceuticals. A particularly preferred filmic material for use as a mold in the present invention is described in WO94/12142. The desired quantities of the suspension or solution may be filled into the mold using an automatic filling means which delivers a predetermined dose into each of the depressions in the mold.

A covering material may be adhered to the filmic material in the area surrounding the depressions after the removal of solvent from the solution or suspension filling the depressions. The covering sheet is preferably an aluminum foil or aluminum foil laminate which may be adhered to the filmic material around the depressions by, for example a heat sensitive material. The cover sheet may be adhered to the filmic material in a manner such that it can be peeled away by the user to uncover the oral dosage form in the depression in the mold or, alternatively, it may be adapted for the oral dosage forms to be pushed through.

Alternative methods of forming discrete frozen or gelled units of the solution or suspension include solidifying the mixtures in dropwise fashion. For example, the solution or suspension may be passed through one or more holes to form drops, spheres or a spray of small particles which can be solidified by passage through a cold gas or liquid, for example liquid nitrogen. Alternatively, the drops, spheres or spray may be solidified by contact with a chilled liquid which is miscible with the solution or suspension and which has a density such that the drops either fall through the miscible liquid as they solidify, or float on the surface of the miscible liquid.

The suspension or solution prepared in accordance with the process of the present invention may also contain other additional ingredients such as coloring agents, flavoring agents, sweetening agents or preservatives, or fillers such as mannitol or sorbitol which improve the physical properties of the oral dosage form.

The product produced by U.S. Pat. No. 5,382,437 to Ecanow is generally dimensionally larger than the product of the present invention. Based on the data appearing in Example 1 of this reference, a product would be produced which has a diameter approximately four to five times larger than the thickness. Thus, for a thickness of about 4 mm, the Ecanow product would have a diameter of about 3 cm. In the present invention, the product is dimensionally smaller and generally has a diameter of about 1 to 1.5 times the thickness of the product. For a thickness of 4 mm, the diameter may be of the order of about 7 mm.

The process of the present invention may be used to prepare rapidly disintegrating dosage forms of various pharmaceutically active substances which have an unacceptable taste. For example, loperamide is incorporated into conventional tablets in the form of its hydrochloride which has an unacceptable taste for formulation into a rapidly disintegrating dosage form. However, the use of loperamide in the form of the free base enables a palatable dosage form to be produced. Similarly, domperidone is incorporated into conventional tablets in the form of its maleate which has an unacceptable taste for formulation into a rapidly disintegrating dosage form. However, the use of domperidone in the form of the free base enables a palatable dosage form to be produced.

An advantage of the use of the less soluble forms of the pharmaceutically active substances in the process of the present invention is that the less soluble forms are generally easier to freeze dry, vacuum dry or dry conventionally.

The process of the present invention for making more palatable rapidly disintegrating dosage forms obviates the need to use costly drug coating techniques or complexation techniques to mask the taste of the pharmaceutically active substance. The present invention will be further described with reference to the following Examples, which are intended to be illustrative and not limitative.

EXAMPLE 1

A solid, oral, rapidly disintegrating dosage form of loperamide was prepared from loperamide hydrochloride using the following ingredients:

| INGREDIENTS | QUANTITIES FOR 400 UNITS |
| --- | --- |
| Loperamide hydrochloride | 0.800 g |
| Gelatin | 2.345 g |
| Mannitol | 1.759 g |
| Aspartame | 0.300 g |
| Mint flavor | 0.120 g |
| Sodium hydrogen carbonate | 0.150 g |
| Purified water | 54.526 g |

The gelatin was added to water in a mixing bowl and heated with mixing to approximately 40° C. The mixture was mixed and homogenized under vacuum until dissolution of the gelatin was complete.

The gelatin solution was added to a mixture of mannitol, sodium hydrogen carbonate and loperamide hydrochloride and the mixture mixed and homogenized until the soluble components had dissolved and the dispersion of the drug particles was complete. The mixture was cooled under vacuum and aspartame and mint flavor added thereto.

The suspension was dosed into blister pockets, frozen and freeze dried to produce the final dosage form. During the processing the loperamide hydrochloride was converted into the less soluble loperamide free base form by the sodium hydrogen carbonate buffer.

The product had an acceptable taste.

EXAMPLE 2

Domperidone maleate is a poor tasting pharmaceutical compound and when initially formulated as a freeze dried rapidly disintegrating oral dosage form, produced an unacceptable product.

Domperidone was formulated in the form of the free base (which is less soluble in water or saliva than domperidone maleate) into a solid, oral, rapidly disintegrating dosage form using the following ingredients.

| INGREDIENTS | WEIGHT PER UNIT |
| --- | --- |
| Domperidone (free base) | 10 mg |
| Aspartame | 0.75 mg |
| Peppermint flavor | 0.15 mg |
| Gelatin | 5.70 mg |
| Mannitol | 5.20 mg |
| Purified water | 128.20 mg |

A solution containing the gelatin and mannitol was prepared and to this was added the aspartame and peppermint flavor. Aliquots of the resulting solution were added to the domperidone powder and a paste formed on stirring. The remainder of the solution was added and homogeneous suspension obtained. The suspension was dispensed in 150 mg aliquots into the pockets of a blister pack, frozen and freeze dried to produce the final dosage form.

The product had an acceptable taste.

EXAMPLE 3

The following is an example of conversion of a salt to a free base. A mixture was formed with the following ingredients:

| INGREDIENTS | WEIGHT PER UNIT |
| --- | --- |
| Loperamide Hydrochloride | 12 g |
| Sodium hydrogen carbonate | 2.5 g |
| Gelatin | 35 g |
| Mannitol | 26 g |
| Water | 825.5 g |

The mixture was agitated mixed using a high shear mixer until the loperamide salt was converted to the free base. This was determined by monitoring the change in crystal morphology using a microscope. The mixture is then dosed into blister pockets, frozen and freeze dried to produce the final dosage form.

EXAMPLE 4

The following is an example conversion of a salt to a free acid. A mixture was formed as follows:

| INGREDIENTS | WEIGHT PER UNIT |
| --- | --- |
| Diclofenac Potassium | 50 g |
| Citric Acid | 50 g |
| Gelatin | 20 g |
| Mannitol | 15 g |
| Water | 365 g |

The mixture was agitated using a high shear mixer until the conversion was completed. This was determined by monitoring the change in crystal morphology using a microscope. The mixture is then dosed into blister pockets, frozen, and freeze dried to produce the final dosage form.

EXAMPLE 5

The following is an example of formation of a hydrate. Hydrates of some drugs have a reduced solubility compared to the anhydrous forms. The formation of a hydrate may be achieved by suspending the drug in an aqueous medium and agitating until the respective hydrate is formed. This process can be accelerated by using heat and a high shear mixing. A suspension was formed using the following ingredients:

| INGREDIENTS | WEIGHT PER UNIT |
| --- | --- |
| Thyroxine sodium | 1 g |
| Water | 500 g |

The suspension was agitated until the thyroxine salt was converted to the hydrate form. This was determined by monitoring the change in crystal morphology using a microscope.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

We claim:

1. A process for the preparation of a solid, oral, rapidly disintegrating dosage form of a pharmaceutically active substance which has an unacceptable taste, which process comprises:
   a) forming a system selected from the group consisting of a solution and a suspension in an aqueous or alcoholic solvent of a form of the pharmaceutically active substance which is rendered less soluble by a method selected from the group consisting of conversion of a salt to a corresponding free acid, conversion of a salt to a corresponding free base, changing the salt form, formation of a hydrate and changing the polymorphic form thereof; together with a carrier material selected from the group consisting of water-soluble and water-dispersible carrier materials;
   b) forming discrete units of the system; and
   c) removing the solvent from the discrete units under conditions whereby a network of the carrier material carrying a dosage of the less soluble and more palatable form of the pharmaceutically active substance is formed.

2. The process according to claim 1 wherein the pharmaceutically active substance with the unacceptable taste is presented in a less soluble form prior to formation of said system.

3. The process according to claim 1 wherein the pharmaceutically active substance with the unacceptable taste is converted into a less soluble form during the preparation of the system.

4. The process according to claim 1 wherein the carrier material is gelatin.

5. The process according to claim 1 wherein the discrete units are selected from the group consisting of liquid, frozen and gelled units.

6. The process according to claim 5 wherein the discrete units are formed in a mold comprising a plurality of pockets.

7. The process according to claim 5 wherein the discrete units are liquid units which are frozen prior to removal of the solvent.

8. The process according to claim 5 wherein the units are frozen units and the solvent is removed by freeze drying.

9. The process according to claim 5 wherein said units are frozen liquid units and said solvent is removed by vacuum drying under conditions whereby the solvent is evaporated from said frozen units through the liquid phase to a gas.

10. The process according to claim 5 wherein the discrete units are gelled units from which the solvent is removed by drying under conditions selected from the group consisting of decreased pressure and forced-air drying.

11. The process according to claim 6 wherein the mold comprises at least one depression in a sheet of a filmic material.

12. The process according to claim 11 wherein a sheet of a covering material is adhered to a filmic material in the area around at least one said depression after the removal of solvent from said system.

13. The process according to claim 1 wherein the pharmaceutically active substance is loperamide hydrochloride which is converted into the form of the loperamide free base during the preparation of the system.

14. The process according to claim 1 wherein the less soluble pharmaceutically active substance is free domperidone base.

15. A solid, oral, rapidly disintegrating dosage form of a pharmaceutically active substance prepared by a process according to claim 1.

16. A solid, oral, rapidly disintegrating dosage form according to claim 15 wherein the pharmaceutically active is loperamide which is present in the composition in the form of the loperamide free base.

17. A solid, oral, rapidly disintegrating dosage form comprising loperamide free base as the pharmaceutically active substance in a network of a carrier material selected from the group consisting of water-soluble and water-dispersible carrier materials.

* * * * *